(12) United States Patent
Yang et al.

(10) Patent No.: US 8,388,673 B2
(45) Date of Patent: Mar. 5, 2013

(54) POLYMERIC STENT

(75) Inventors: Arlene Sucy Yang, Belmont, CA (US);
Kevin Jow, San Mateo, CA (US);
Andrea Dawn Morrison, San Mateo, CA (US); Timothy A. Limon, Cupertino, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 441 days.

(21) Appl. No.: 12/557,758

(22) Filed: Sep. 11, 2009

(65) Prior Publication Data

US 2010/0004735 A1  Jan. 7, 2010

Related U.S. Application Data

(63) Continuation-in-part of application No. 12/114,608, filed on May 2, 2008, now Pat. No. 8,002,817.

(51) Int. Cl.
*A61F 2/06* (2006.01)
(52) U.S. Cl. ........................ 623/1.15; 623/1.14; 623/1.16
(58) Field of Classification Search ........ 623/1.14–1.16, 623/1.34
See application file for complete search history.

(56) References Cited

U.S. PATENT DOCUMENTS

| | | | |
|---|---|---|---|
| 5,514,154 A | 5/1996 | Lau et al. | |
| 5,741,327 A * | 4/1998 | Frantzen | 623/1.34 |
| 6,206,911 B1 * | 3/2001 | Milo | 623/1.15 |
| 6,273,910 B1 * | 8/2001 | Limon | 623/1.15 |
| 6,312,459 B1 | 11/2001 | Huang et al. | |
| 6,616,689 B1 * | 9/2003 | Ainsworth et al. | 623/1.16 |
| 6,758,859 B1 * | 7/2004 | Dang et al. | 623/1.15 |
| 7,273,492 B2 * | 9/2007 | Cheng et al. | 623/1.11 |
| 7,273,495 B2 * | 9/2007 | Limon | 623/1.15 |
| 8,206,436 B2 * | 6/2012 | Mangiardi et al. | 623/1.46 |
| 8,211,163 B2 * | 7/2012 | Dakin et al. | 623/1.15 |
| 2003/0023301 A1 | 1/2003 | Cox et al. | |
| 2004/0044400 A1 * | 3/2004 | Cheng et al. | 623/1.16 |
| 2006/0020330 A1 | 1/2006 | Huang et al. | |
| 2006/0076708 A1 | 4/2006 | Huang et al. | |
| 2006/0265050 A1 | 11/2006 | Morris et al. | |

(Continued)

FOREIGN PATENT DOCUMENTS

| | | |
|---|---|---|
| EP | 1 859 823 | 11/2007 |
| EP | 2 152 207 | 11/2008 |

(Continued)

OTHER PUBLICATIONS

European Search Report for appl. No. 08 747619.8, mailed Sep. 27, 2011, 5 pgs.

(Continued)

*Primary Examiner* — Thomas J Sweet
*Assistant Examiner* — Seema Mathew
(74) *Attorney, Agent, or Firm* — Squire Sanders (US) LLP

(57) ABSTRACT

A strut pattern of an endoprosthesis includes a plurality of W-shape cells that define a tubular body, the W-shaped cells at the opposite ends of the tubular body have a modified configuration that is different than the W-shaped cells at the middle portion of the tubular body. At the distal end of the tubular body, the W-shaped cells have crests with axial positions that are axially spaced apart, and have troughs with circumferential positions that are spaced apart. At the intermediate and distal end of the tubular body, the W-shaped cells crests with axial positions that coincide and have troughs with circumferential positions that coincide. The strut pattern is cut from a tubular precursor construct made of PLLA that has been radially expanded and axially extended by blow molding.

20 Claims, 11 Drawing Sheets

U.S. PATENT DOCUMENTS

| | | |
|---|---|---|
| 2007/0271763 A1 | 11/2007 | Huang et al. |
| 2007/0293938 A1 | 12/2007 | Gale et al. |
| 2008/0275537 A1 | 11/2008 | Limon |
| 2011/0230959 A1 | 9/2011 | Pienknagura |

FOREIGN PATENT DOCUMENTS

| | | |
|---|---|---|
| WO | WO 2007/021706 | 2/2007 |
| WO | WO 2007/142750 | 12/2007 |
| WO | WO 2007/146354 | 12/2007 |
| WO | WO 2007/149457 | 12/2007 |

OTHER PUBLICATIONS

International Search Report for PCT/US2008/062607, mailed Aug. 5, 2008, 6 pgs.

\* cited by examiner

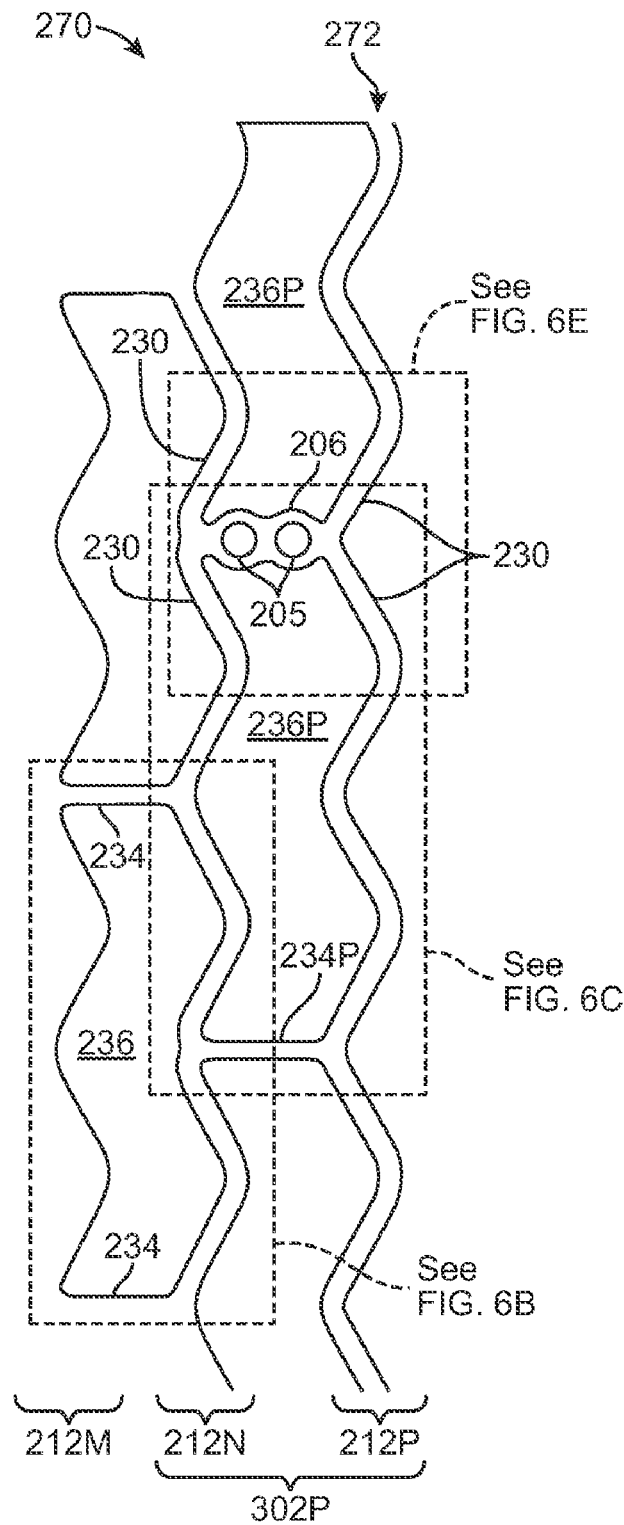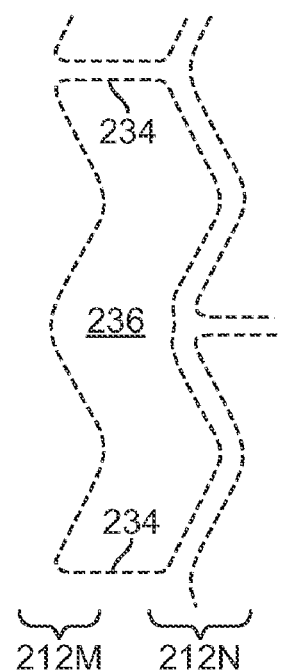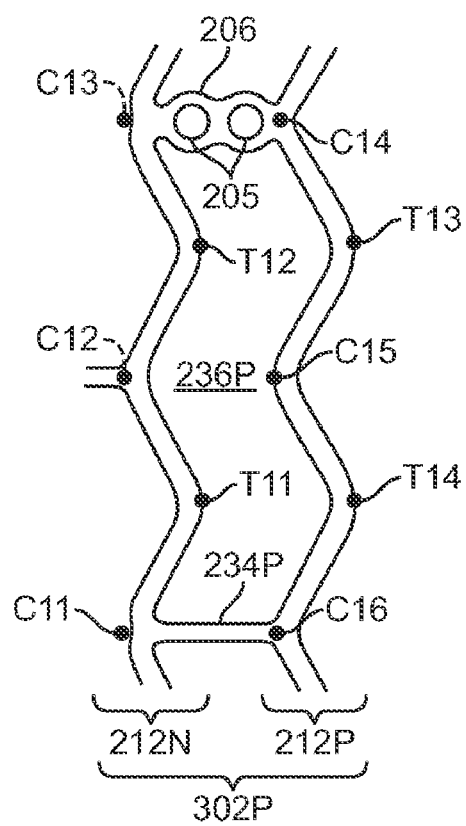
FIG. 6A
FIG. 6B
FIG. 6C

POLYMERIC STENT

CROSS-REFERENCE TO RELATED APPLICATION

The present application is a continuation-in-part of application Ser. No. 12/114,608, filed May 2, 2008 now U.S. Pat. No. 8,002,817, the entire disclosure of which is incorporated herein by reference.

FIELD OF THE INVENTION

Briefly and in general terms, the present invention generally relates to coating a medical device, more specifically, to a system and method for coating a stent.

BACKGROUND OF THE INVENTION

In percutaneous transluminal coronary angioplasty (PTCA), a balloon catheter is inserted through a brachial or femoral artery, positioned across a coronary artery occlusion, and inflated to compress against atherosclerotic plaque to open, by remodeling, the lumen of the coronary artery. The balloon is then deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical bypass operation. Stents are used to address these issues. Stents are small, intricate, implantable medical devices and are generally left implanted within the patient to reduce occlusions, inhibit thrombosis and restenosis, and maintain patency within vascular lumens such as, for example, the lumen of a coronary artery.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

For example, FIG. 7 shows an upper portion of a stent 10 having an overall body shape that is hollow and tubular. The stent can be made from wires, fibers, coiled sheet, with or without gaps, or a scaffolding network of rings. The stent can have any particular geometrical configuration, such as a sinusoidal or serpentine strut configuration, and are not limited to what is illustrated in FIG. 7. The variation in strut patterns is virtually unlimited. The stent can be balloon expandable or self-expandable, both of which are well known in the art.

FIGS. 7 and 8 show stents with two different strut patterns. The stents are illustrated in an uncrimped or expanded state. In both FIGS. 7 and 8, the stent 10 includes many interconnecting struts 12, 14 separated from each other by gaps 16. The struts 12, 14 can be made of any suitable material, such as a biocompatible metal or polymer. The stent 10 has an overall longitudinal length 40 measured from opposite ends, referred to as the distal and proximal ends 22, 24. The stent 10 has an overall body 50 having a tube shape with a central passageway 17 passing through the entire longitudinal length of the stent. The central passageway has two circular openings, there being one circular opening at each of the distal and proximal ends 22, 24 of the overall tubular body 50. A central axis 18 runs through the central passageway in the center of the tubular body 50. At least some of the struts 12 are arranged in series to form sinusoidal or serpentine ring structures 20 that encircle the central axis 18.

FIG. 9 is an exemplary cross-sectional view of the stent 10 along line 9-9 in FIG. 8. There can be any number of struts 12, 14 along line 9-9. Line 9-9 runs perpendicular to the central axis 18 of the stent 10. In FIG. 9, the cross-section of seven struts 12, 14 are shown for ease of illustration. The struts 12, 14 in cross-section are arranged in a circular pattern having an outer diameter 26 and an inner diameter 28. The circular pattern encircles the central axis 18. A portion of the surface of each strut faces radially inward in a direction 30 facing toward the central axis 18. A portion of the surface of each strut faces radially outward in a direction 32 facing away from the central axis 18. The various strut surfaces that face radially outward collectively form the outer surface 34 of the stent 10. The various strut surfaces that face radially inward collectively form the inner surface 36 of the stent 10.

The terms "axial" and "longitudinal" are used interchangeably and relate to a direction, line or orientation that is parallel or substantially parallel to the central axis of a stent or a central axis of a cylindrical structure. The terms "circumferential" and "circumferentially" relate to a direction along a circumference of a stent or a circular structure. The terms "radial" and "radially" relate to a direction, line or orientation that is perpendicular or substantially perpendicular to the central axis of a stent or a central axis of a cylindrical structure.

Stents are often modified to provide drug delivery capabilities to further address thrombosis and restenosis. Stents may be coated with a polymeric carrier impregnated with a drug or therapeutic substance. A conventional method of coating includes applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer.

The stent must be able to satisfy a number of functional requirements. The stent must be capable of withstanding the structural loads, namely radial compressive forces, imposed on the stent as it supports the walls of a vessel after deployment. Therefore, a stent must possess adequate radial strength. Radial strength, which is the ability of a stent to resist radial compressive forces, is due to strength and rigidity around a circumferential direction of the stent. After deployment, the stent must also adequately maintain its size and shape throughout its service life despite the various forces that may come to bear on it, including the cyclic loading induced by the beating heart.

In addition to high radial strength, the stent must also possess sufficient flexibility to allow for crimping on the a delivery device, flexure during delivery through an anatomical lumen, and expansion at the treatment site. Longitudinal flexibility is important to allow the stent to be maneuvered through a tortuous vascular path and to enable it to conform to a deployment site that may not be linear or may be subject to flexure. A stent should have sufficient toughness so that it is resistant to crack formation, particularly, in high strain regions during crimping, delivery, and deployment.

Furthermore, it may be desirable for a stent to be made of a biodegradable or bioerodable polymer. It is believed that biodegradable stents allow for improved healing of the anatomical lumen as compared to metal stents, which may lead to a reduced incidence of late stage thrombosis.

However, a potential shortcoming of polymer stents compared to metal stents of the same dimensions, is that polymer stents typically have less radial strength and rigidity. Relatively low radial strength potentially contributes to relatively high recoil of polymer stents after implantation into an anatomical lumen. "Recoil" refers to the undesired retraction of a stent radially inward from its deployed diameter due to radially compressive forces that bear upon it after deployment. Another potential problem with polymer stents is that struts can crack or fracture during crimping, delivery and deployment, especially for brittle polymers.

Some crystalline or semi-crystalline polymers that may be suitable for use in implantable medical devices generally have potential shortcomings with respect to some mechanical characteristics, in particular, fracture toughness, when used in stents. Some polymers, such as poly(L-lactide) ("PLLA"), are stiff and strong but can exhibit a brittle fracture mechanism at physiological conditions in which there is little or no plastic deformation prior to failure. A stent fabricated from such polymers can have insufficient toughness for the range of use of a stent. As a result, cracks, particularly in high strain regions, can be induced which can result in mechanical failure of the stent.

Stent performance may be measured in terms of the number of cracks or broken struts after crimping and deployment. Stent performance may be affected by complex interaction of many factors related to processing of the tubular construct out of which the strut pattern is formed, polymer material composition, polymer material morphology and microstructure, and the geometry and dimensions of the strut pattern itself. Factors related processing of the tubular construct include those associated with extrusion and subsequent blow molding as described in U.S. patent application Ser. No. 11/771,967, filed Jun. 29, 2007, "Method of Manufacturing a Stent from a Polymer Tube," the contents of which are incorporated herein by reference. Processing factors that affect stent performance include without limitation draw down ratio during extrusion, blow molding temperature relative to glass transition temperature of the polymer, blow molding pressure used to expand the polymer tube, radial expansion ratio during blow molding, and axial extension during blow molding. These processing factors are used to modify the crystalline morphology and polymer chain orientation to achieve a desired combination of strength and fracture toughness along axial and radial directions.

There is a continuing need strut designs and manufacturing methods for fabricating polymeric stents that impart sufficient radial strength, fracture toughness, low recoil, and sufficient shape stability.

SUMMARY OF THE INVENTION

Briefly and in general terms, the present invention is directed to an endoprosthesis having a plurality of struts forming W-shape closed cells.

In aspects of the present invention, an endoprosthesis comprises a tubular body formed of a polymer. The tubular body includes an end segment and an intermediate segment adjoining the end segment. The end segment includes a circumferential series of closed cells having a first W-shape. The intermediate segment includes a circumferential series of closed cells having a second W-shape. There are linear link struts at opposite ends of the individual first and second W-shapes. The linear link struts of the first W-shape are longer than linear link struts of the second W-shape.

In further aspects, one of the linear link struts within the end segment is a marker strut that includes one or more holes. In detailed aspects, a closed cell immediately adjacent to one side of the marker strut is a mirror image or is substantially a mirror image of a closed cell immediately adjacent to the opposite side of the marker strut. In other detailed aspects, a first cell from among the closed cells of the end segment includes a first crest at one end of the marker strut and a second crest circumferentially adjacent the first crest, the first crest having an axial position that is axially spaced apart from the axial position of the second crest. In further detailed aspects, the first cell includes a third crest circumferentially adjacent the second crest, the second crest is located between the first and third crests, and the first and third crests have axial positions that coincide.

In other aspects of the present invention, an endoprosthesis comprises ring structures made of polymer material. The ring structures form a tubular body having a distal end, a proximal end, and an intermediate segment between the distal and proximal ends. The ring structures are connected to each other by linear link struts that are oriented axially. The ring structures and link struts form W-shape closed cells. The W-shape closed cells include nominal cells within the intermediate segment of the tubular body and end cells at the distal and proximal ends of the tubular body. The linear link struts of the end cells are axially longer than the linear link struts of the nominal cells.

In detailed aspects, each end cell at the distal end of the tubular body is bounded by a distal pair of ring structures, wherein each end cell at the distal end includes two crests that are located on one of the distal pair of ring structures and have axial positions that are axially spaced apart from each other, and wherein each end cell at the distal end further includes three crests that are located on the other one of the distal pair of end ring structures and have axial positions that coincide.

In other detailed aspects, each nominal cell is bounded by an intermediate pair of ring structures, wherein each nominal cell includes three crests that are located on one of the intermediate pair of ring structures and have axial positions that coincide, and further includes three crests that are located on the other one of the intermediate pair of ring structures and have axial positions that coincide.

In further detailed aspects, each end cell at the proximal end of the tubular body is bounded by a proximal pair of ring structures, wherein each end cell at the proximal end includes three crests that are located on one of the proximal pair of ring structures and have axial positions that coincide, and wherein each end cell at the proximal end further includes three crests that are located on the other one of the proximal pair of ring structures and have axial positions that coincide.

The features and advantages of the invention will be more readily understood from the following detailed description which should be read in conjunction with the accompanying drawings.

BRIEF DESCRIPTION OF THE DRAWINGS

FIGS. 6A-6C and 6E are detailed views of a proximal portion of the strut pattern of FIG. 2.

DETAILED DESCRIPTION OF THE PREFERRED EMBODIMENTS

Figure 1:
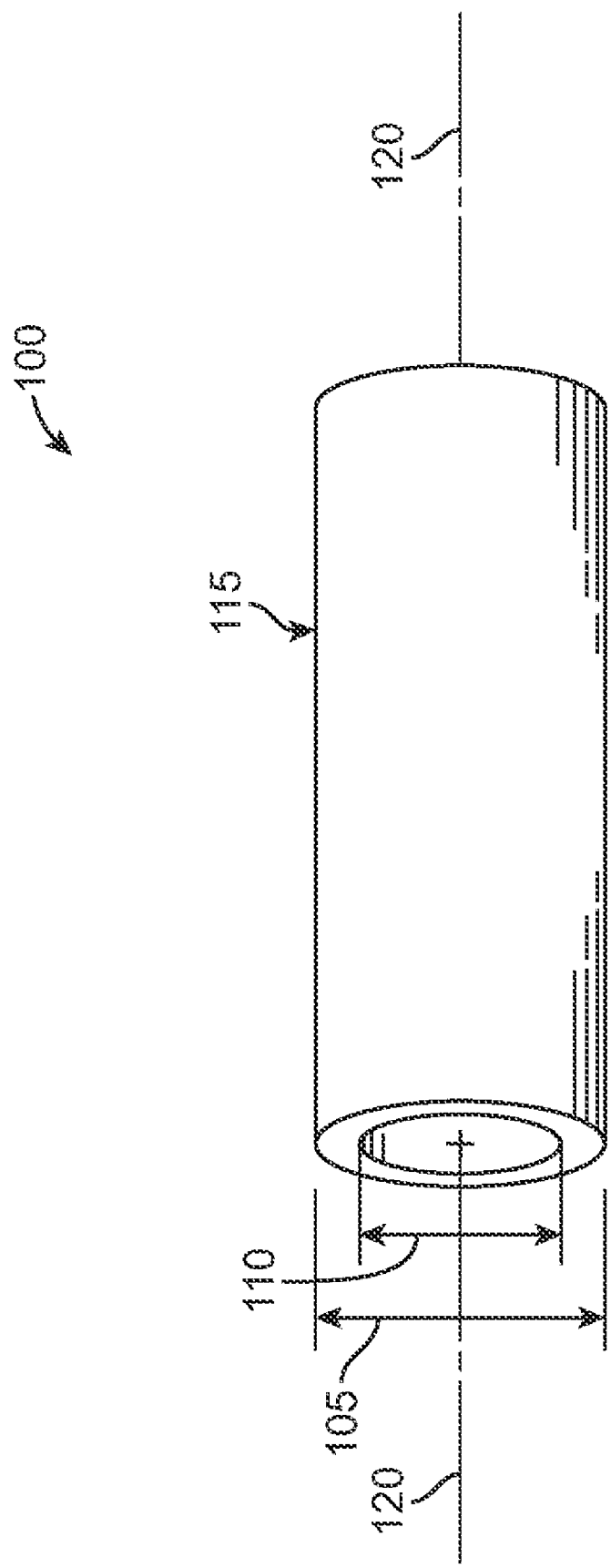
FIG. 1 is a perspective view of a tubular precursor construct for a polymer stent.

Referring now in more detail to the exemplary drawings for purposes of illustrating embodiments of the invention, wherein like reference numerals designate corresponding or like elements among the several views, there is shown in FIG. 1 a tube 100 that serves as a stent precursor construct in the sense that further processing is performed on the tube before the pattern of stent struts is cut formed from the tube.

After further processing of the tube 100, a pattern of struts is formed on the resultant tube by chemical etching, mechanical cutting, or laser cutting material away from the tube. Representative examples of lasers that may be used include without limitation excimer, carbon dioxide, YAG, and ultra fast lasers. The tube 100 is cylindrically-shaped with an outside diameter 105, an inside diameter 110, an outside surface 115, and a central axis 120.

The tube 100 is formed by extrusion of poly(L-lactide) ("PLLA"). In other embodiments, a tubular precursor construct is formed by injection molding or rolling a cast flat sheet of material to form a tube, and may be made of other polymer materials including without limitation poly(lactic-co-glycolic acid) ("PLGA"). Deformation, the resulting crystal morphology of the polymer matrix, the preferential orientation of polymer molecule chains within the polymer matrix, and, thus, the mechanical properties of the tubular precursor construct, are dependant on whether the injection molding, extrusion, or casting is performed.

During extrusion, a polymer melt of is conveyed through an extruder which is then formed into a tube. Extrusion tends to impart large forces on the polymer molecules in the longitudinal direction of the tube due to shear forces on the polymer melt. The shear forces arise from forcing the polymer melt through an opening of a die at the end of an extruder. Additional shear forces may arise from any pulling and forming of the polymer melt upon exiting the die, such as may be performed in order to bring the extruded material to the desired dimensions of a finished tube. As a result, polymer tubes formed by some extrusion methods tend to possess a significant degree of molecular and/or crystal orientation in the direction that the polymer is extruded with a relatively low degree of orientation in the circumferential direction, thereby affecting the mechanical properties, such as strength and toughness, of the extruded tube.

The degree of pulling that is applied to the polymer melt as it exits a die of an extruder and, thus, the degree of longitudinal orientation induced in the finished tube 100 can be partially characterized by what is referred to as a "draw down ratio." Typically, the polymer melt is in the form of an annular film as it is extruded through and exits an annular opening of the die. The annular film has an initial outer diameter upon exiting the annular opening. The annular film is drawn or pulled, which causes a reduction of the annular film cross-sectional size to the final outer diameter 105 (FIG. 1). The drawn down portion of the tube may be actively cooled to ensure that it maintains its shape and diameter. The draw down ratio is defined as the ratio of the final outer diameter to the initial outer diameter.

The finished, solidified polymeric tube 100 made of poly (L-lactide), shown in FIG. 1, is then deformed in radial and axial directions by a blow molding process wherein deformation occurs progressively at a predetermined longitudinal speed along the longitudinal axis of the tube. For example and without limitation, blow molding can be performed as described in U.S. Publication No. 2009/0001633 of patent application Ser. No. 11/771,967, filed Jun. 29, 2007, "Method of Manufacturing a Stent from a Polymer Tube." The deformation improves the mechanical properties of the tube 100. The degree of radial expansion that the polymer tube undergoes can partially characterize the degree of induced circumferential molecular or crystal orientation as well as strength in a circumferential direction. The degree of radial expansion is quantified by a radial expansion ("RE") ratio, defined as RE Ratio=(Inside Diameter of Expanded Tube)/(Original Inside Diameter of the tube). The RE ratio can also be expressed as a percentage, defined as RE %=(RE ratio−1)×100%. The degree of axial extension that the polymer tube undergoes can partially characterize induced axial molecular or crystal orientation as well as strength in an axial direction. The degree of axial extension is quantified by an axial extension ("AE") ratio, defined as AE Ratio=(Length of Extended Tube)/(Original Length of the Tube). The AE ratio can also be expressed as a percentage, defined as AE %=(AE ratio−1)×100%.

The blow molding of the tube 100 produces what is referred to as a "deformed tube" or "blow molded tube." The phrases "deformed tube" or "blow molded tube" are used interchangeably.

Figure 2:
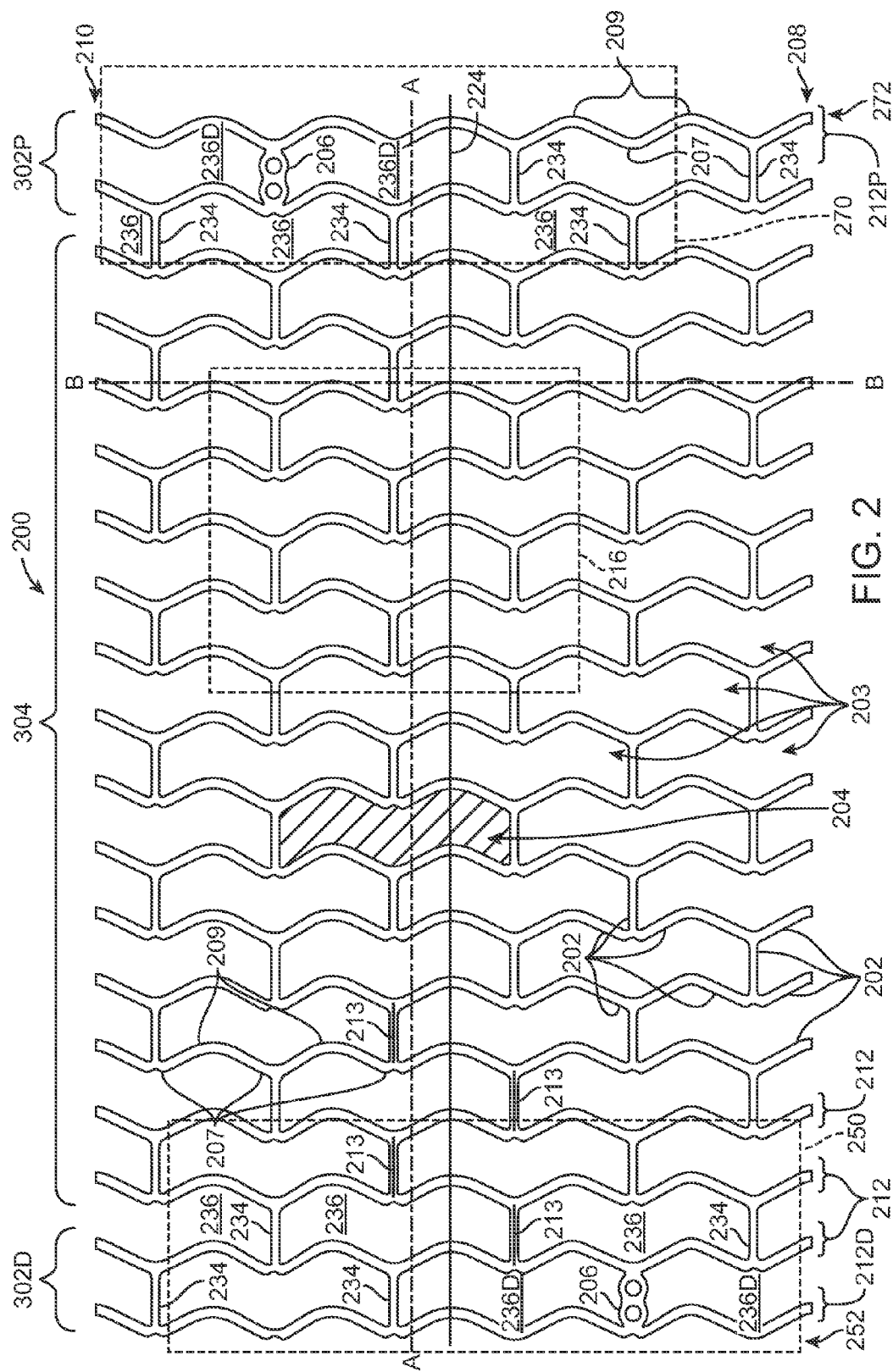
FIG. 2 depicts a strut pattern viewed in a flat or planar state.
Figure 3:
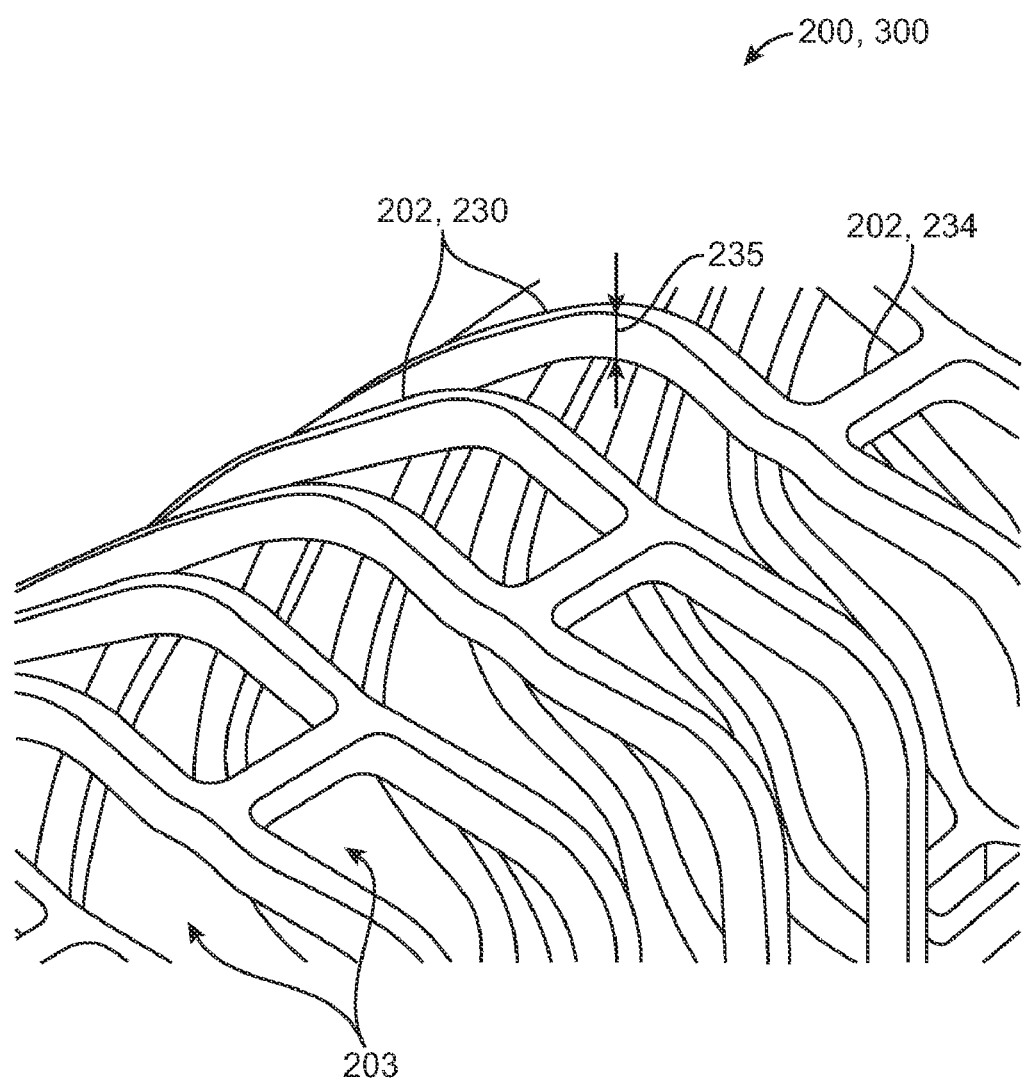
FIG. 3 is a partial perspective view of a stent in an expanded or pre-crimped state, the stent having the strut pattern of FIG. 2.

After blow molding, pieces of the blow molded tube are cut away, leaving stent struts having the pattern 200 shown in FIG. 2. The strut pattern 200 is illustrated in a planar or flattened view for ease of illustration and clarity, and is representative of the pattern of struts before the stent is crimped or after the stent is deployed. The strut pattern 200 actually forms a tubular stent structure, as partially shown in FIG. 3, so that line A-A is parallel to the central axis 224 of the stent. FIG. 3 shows the stent in a state prior to crimping or after deployment. As can be seen from FIG. 3, the stent comprises an open framework of struts that define a generally tubular body.

The strut pattern 200 includes various struts 202 oriented in different directions and gaps 203 between the struts. Each gap 203 and the struts 202 immediately surrounding the gap defines a closed cell 204. At the proximal and distal ends of the stent, a marker strut 206 includes depressions, blind holes, or through holes adapted to hold a radiopaque marker that allows the position of the stent inside of a patient to be determined. One of the closed cells 204 is shown with cross-hatch lines to illustrate the shape and size of the cells.

The pattern 200 is illustrated with a bottom edge 208 and a top edge 210. On a stent, the bottom edge 208 meets the top edge 210 so that line B-B forms a circle around the stent central axis. In this way, the strut pattern 200 forms sinusoidal hoops or rings 212 that include a group of struts arranged circumferentially. The rings 212 include a series of crests 207 and troughs 209 that alternate with each other. The sinusoidal variation of the rings 212 occurs primarily in the axial direction, not in the radial direction. That is, all points on the outer surface of each ring 212 are at the same or substantially the same radial distance away from the central axis of the stent.

Still referring to FIG. 2, the rings 212 are connected to each other by another group of struts that have individual lengthwise axes 213 parallel or substantially parallel to line A-A. The rings 212 are capable of being collapsed to a smaller diameter during crimping and expanded to their original diameter or to a larger diameter during deployment in a vessel.

Figure 4:
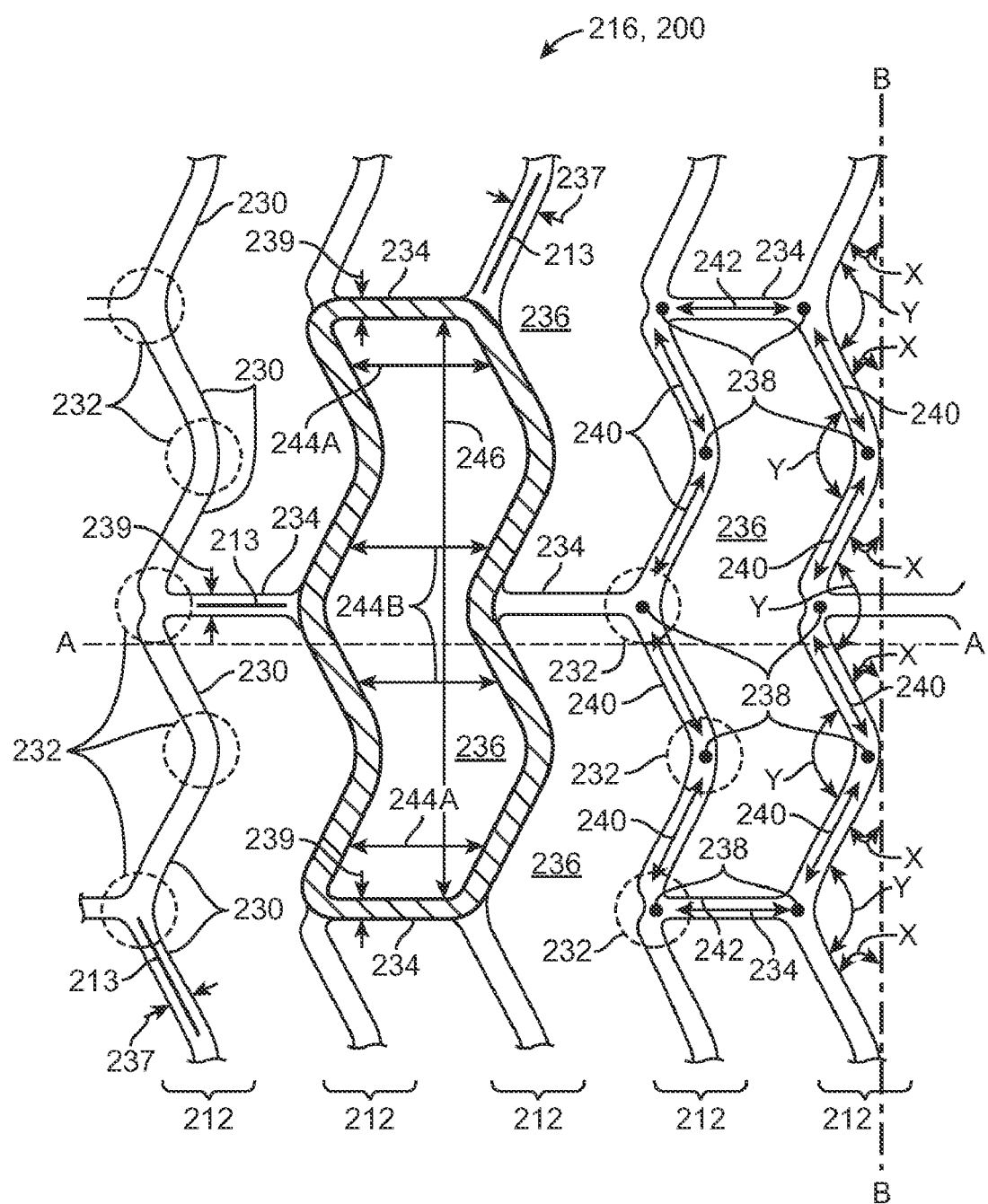
FIG. 4 is a detailed view of an intermediate portion of the strut pattern of FIG. 2.

FIG. 4 shows a detailed view of an intermediate portion 216 of the strut pattern 200 of FIG. 2. The intermediate portion 216 is located between the distal and proximal end rings of the stent. The rings 212 include linear ring struts 230 and curved hinge elements 232. The ring struts 230 are connected to each other by the hinge elements 232.

The hinge elements 232 are adapted to flex, which allows the rings 212 to move from a non-deformed configuration to a deformed configuration. As used herein in connection with the strut pattern 200, "non-deformed configuration" refers to the state of the rings prior to being crimped to a smaller diameter for delivery through an anatomical lumen. As used herein in connection with the strut pattern 200, "deformed configuration" refers to the state of the rings upon some type of deformation, such as crimping or deployment to a diameter greater than the original diameter prior to crimping.

Still referring to FIG. 4, line B-B lies on a reference plane perpendicular to the central axis 224 (FIG. 2). When the rings 712 are in the non-deformed configuration, as shown in FIG. 4, each ring strut 730 is oriented at a non-zero angle X relative to the reference plane. The non-zero angle X is between 20 degrees and 30 degrees, and more narrowly at or about 25 degrees. In other embodiments, the angle X can have other values.

Also, the ring struts 230 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the stent is deployed. Having the interior angle be less than 180 degrees allows the stent to be crimped while minimizing damage to the stent struts during crimping, and may also allow for expansion of the stent to a deployed diameter that is greater than its initial diameter prior to crimping. In other embodiments, the interior angle Y can have other values.

Referring once again to FIG. 4, the stent also includes link struts 234 connecting the rings 212 together. The link struts 234 are oriented parallel or substantially parallel to line A-A and the central axis 224 (FIG. 2). The ring struts 230, hinge elements 232, and link struts 234 define a plurality of W-shape closed cells 236. The boundary or perimeter of one W-shape closed cell 236 is darkened in FIG. 4 for clarity. In FIG. 4, the W-shapes appear rotated 90 degrees counterclockwise. Each of the W-shape closed cells 236 is immediately surrounded by six other W-shape closed cells 236, meaning that the perimeter of each W-shape closed cell 236 merges with a portion of the perimeter of six other W-shape closed cells 236. Each W-shape closed cell 236 abuts or touches six other W-shape closed cells 236.

The perimeter of each W-shape closed cell 236 includes eight of the ring struts 230, two of the link struts 234, and ten of the hinge elements 232. Four of the eight ring struts form a proximal side of the cell perimeter and the other four ring struts form a distal side of the cell perimeter. The opposing ring struts on the proximal and distal sides are parallel or substantially parallel to each other.

Within each of the hinge elements 232 there is an intersection point 238 toward which the ring struts 230 and link struts 234 converge. There is an intersection point 238 adjacent each end of the ring struts 230 and link struts 234. Distances 240 between the intersection points adjacent the ends of rings struts 230 are the same or substantially the same for each ring strut 230 in the intermediate portion 216 of the strut pattern 200. The distances 242 are the same or substantially the same for each link strut 234 in the intermediate portion 216.

The ring struts 230 have widths 237 that are uniform in dimension along the individual lengthwise axis 213 of the ring strut. The ring strut widths 234 are between 0.15 mm and 0.18 mm, and more narrowly at or about 0.165 mm. The link struts 234 have widths 239 that are also uniform in dimension along the individual lengthwise axis 213 of the link strut. The link strut widths 239 are between 0.11 mm and 0.14 mm, and more narrowly at or about 0.127 mm. The ring struts 230 and link struts 234 have the same or substantially the same thickness 235 (FIG. 3) in the radial direction, which is between 0.10 mm and 0.18 mm, and more narrowly at or about 0.152 mm.

As shown in FIG. 4, the interior space of each W-shape closed cell 236 has an axial dimension 244 parallel to line A-A and a circumferential dimension 246 parallel to line B-B. The axial dimension 244 is constant or substantially constant with respect to circumferential position within each W-shape closed cell 236 of the intermediate portion 216. That is, axial dimensions 244A adjacent the top and bottom ends of the cells 236 are the same or substantially the same as axial dimensions 244B further away from the ends. The axial and circumferential dimensions 244, 246 are the same among the W-shape closed cells 236 in the intermediate portion 216.

It will be appreciated that FIG. 4 that the strut pattern for a stent that comprises linear ring struts 230 and linear link struts 234 formed from a radially expanded and axially extended polymer tube. The ring struts 230 define a plurality of rings 212 capable of moving from a non-deformed configuration to a deformed configuration. Each ring has a center point, and at least two of the center points define the stent central axis. The link struts 234 are oriented parallel or substantially parallel to the stent central axis. The link struts 234 connect the rings 212 together. The link struts 232 and the ring struts 230 defining W-shape closed cells 236. Each W-shaped cell 236 abuts other W-shaped cells. The ring struts 230 and hinge elements 232 on each ring 212 define a series of crests 207 and troughs 209 (FIG. 1) that alternate with each other. Each crest 207 on each ring 212 is connected by one of the link struts 234 to another crest on an immediately adjacent ring, thereby forming an offset "brick" arrangement of the W-shaped cells.

In some embodiments, radial expansion of a tube 100 (FIG. 1) by blow molding has reoriented or induced the polymer molecule chains of the tube to be preferentially oriented circumferentially or biaxially, thereby reducing the degree of axial orientation. With biaxial orientation, the polymer molecule chains are oriented in a direction that is neither preferentially circumferential nor preferentially axial. Having reduced the degree of axial orientation, polymer molecule chains in the linear ring struts 230 are preferentially oriented in a direction parallel or substantially parallel to the lengthwise axis 213 of individual ring struts 230 so as to increase the circumferential strength, also referred as hoop strength, of the tubular stent structure. Hoop strength is a physical property that describes the ability of the tubular stent structure to withstand crushing forces directed radially inward. Although reduced axial orientation of polymer molecule chains in the linear ring struts 230 has some advantages, care must also be taken not to reduce axial orientation to such a degree that the axially oriented link struts 234 are unduly weakened.

FIG. 5A-5D show a distal portion 250 (FIG. 2) of the strut pattern 200 immediately adjacent the stent distal end 252. FIGS. 6A-6D show a proximal portion 270 (FIG. 2) of the strut pattern 200 immediately adjacent the stent proximal end 272. FIGS. 5A-5D and 6A-6D show shape variations between the W-shape closed cells 236 in the intermediate portion 216, on one hand, and the W-shape closed cells 236D, 236P at the distal and proximal ends 252, 270, on the other hand.

Figure 5A:
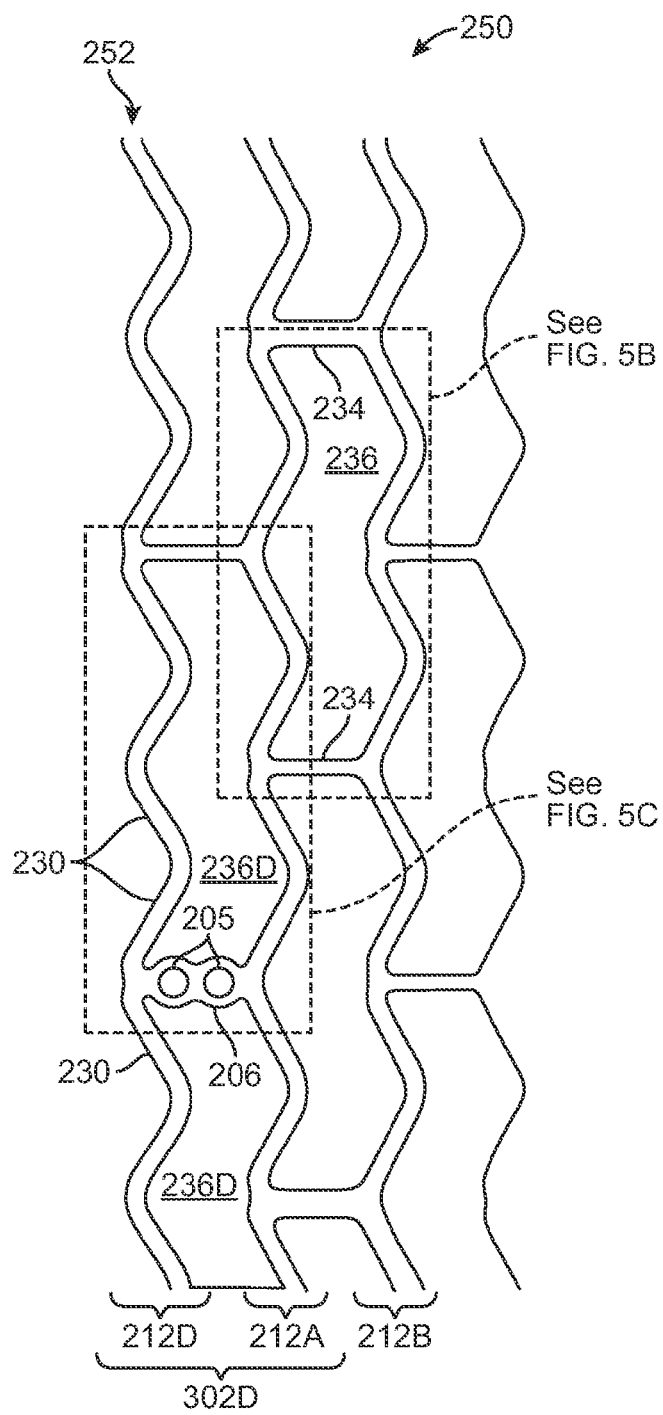
FIGS. 5A-5C are detailed views of a distal portion of the strut pattern of FIG. 2.
Figure 5B:
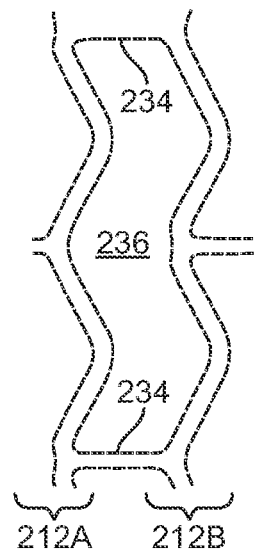

Referring more particularly to FIG. 5B, the W-shape closed cell 236 is bounded in part by two rings 212A, 212B adjacent the most distal ring 212D at the distal edge of the strut pattern 200. The nominal W-shape closed cell 236 in FIG. 5B has the same or substantially the same shape, dimensions, interior angles, and radii as the W-shape closed cells in the intermediate portion 216 of FIG. 4.

Figure 5C:
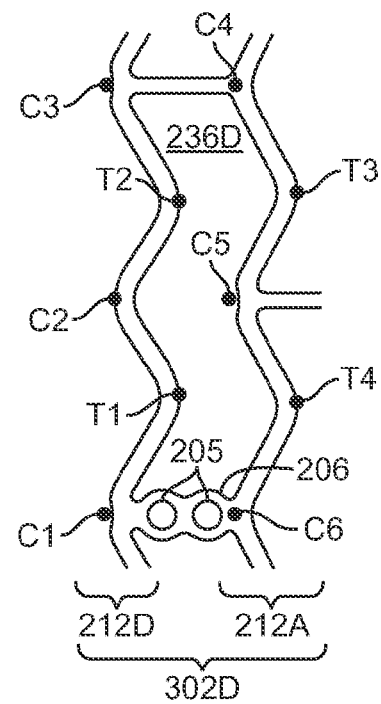

FIG. 5C shows a distal W-shape closed cell 236D bounded in part by the most distal ring 212D, the immediately adjacent ring 212A, and the marker strut 206 configured with two holding elements 205 for carrying a radiopaque marker. The holding elements 205 may be depressions, blind holes, or through holes sized to retain a radiopaque marker bead.

The distal W-shape closed cells 236D directly above and directly below the marker strut 206 are symmetrical about the marker strut. The distal W-shape closed cells 236D directly above and directly below the marker strut 206 are also mirror images of each other, having the same or substantially the same shape, dimensions, interior angles, and radii.

Figure 5D:
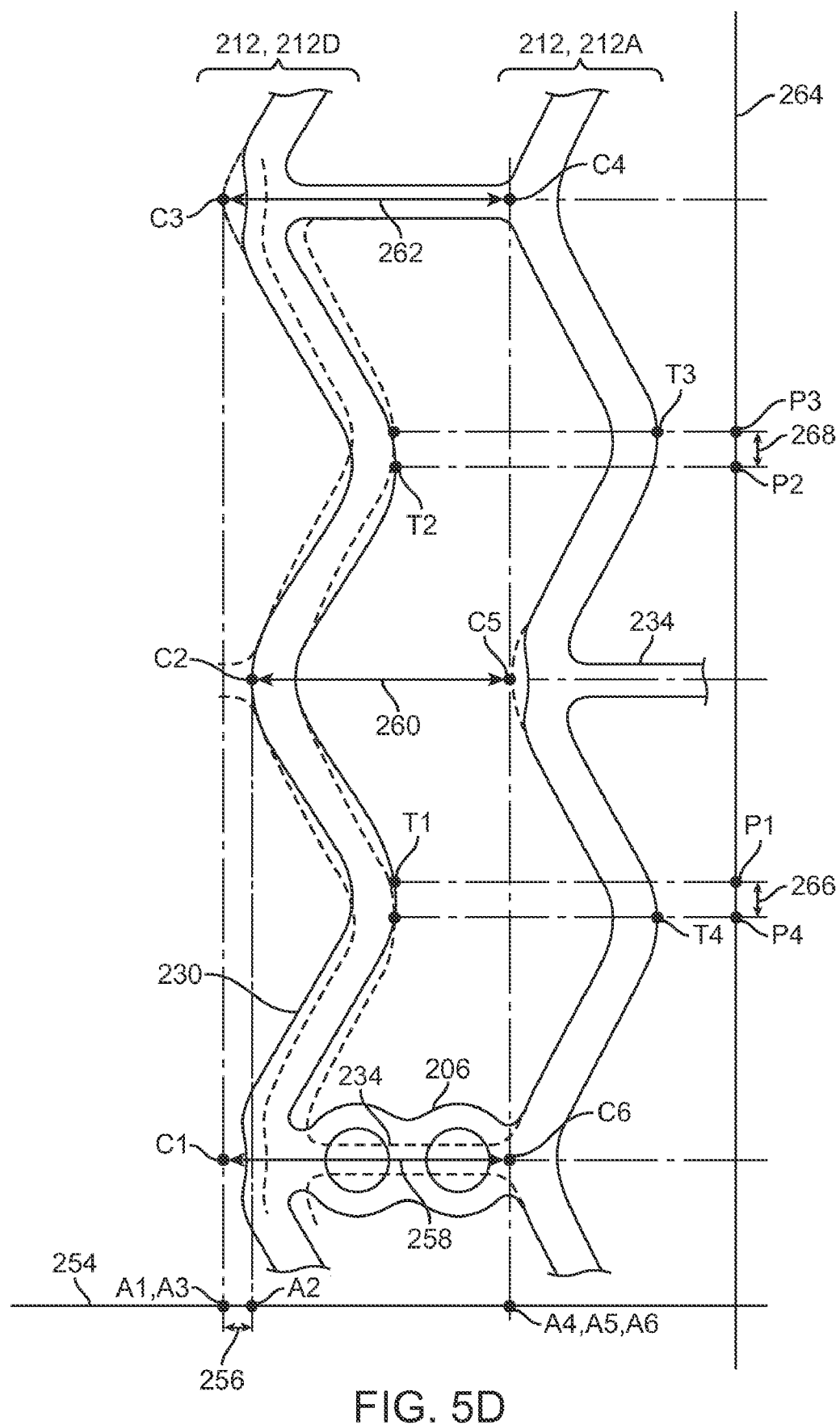
FIG. 5D is a detailed view of the strut pattern portions shown in FIGS. 5B and 5C superimposed over each other.

FIG. 5D shows the W-shape closed cells in FIGS. 5B and 5C superimposed. The struts forming the boundary of the nominal W-shape closed cell 236 in FIG. 5C are illustrated in dashed line in FIG. 5D to better show differences from the distal W-shape closed cell 236D. It will be appreciated that the marker strut 206 of the distal W-shape closed cell 236D has a longer axial dimension than link struts 234 of the nominal W-shape closed cell 236.

In some embodiments, the size of the marker bead is driven by the minimum amount of radiopaque material needed to visualize the marker. The size of the holes 205 depends upon the size of the marker beads. The polymeric material of the marker strut 206 must be of sufficient width to avoid cracking when the marker beads are inserted into the holes 205, one at a time, during manufacturing. The required width of the polymeric material around the holes 205 may, in turn, determine the length of the marker strut. The length of the link struts 234, in some embodiments, is determined by the amount of desired flexure and fracture toughness during crimping, delivery, and deployment.

With continued reference to FIG. 5D, an axial line 254 is illustrated for reference in order to show the relative axial positions of various structural elements. The axial line 254 is parallel or substantially parallel to the central axis of the stent. The approximate locations of the crests for the distal W-shape closed cell 236D are individually designated in clockwise order as C1, C2, C3, C4, C5, and C6. Crests C1, C3 and C5 are approximated by dotted curved lines which have the same or substantially the same radius as that at crest C2. The respective axial positions of the crests are indicated on the axial line 254 as A1, A2, A3, A4, A5, and A6. The axial positions A1 and A3 of crests C1 and C3 coincide with each other and are axially offset by a distance 256 from crest C2 located circumferentially between crests C1 and C3. The axial positions A4, A5 and A6 of crests C4, C5 and C6 coincide with each other.

In some embodiments, the offset distances 256, 266, 268 is determined by several considerations. A first consideration is the need to keep the circumference of the end rings 212D, 212P the same as the circumference of the adjacent rings 212A, 212B, 212M, 212N (FIGS. 5A and 6A). A second consideration is that the addition of the marker struts 206 makes the transition to the ring struts 230 difficult while avoiding tight (i.e., small) radii and high stress associated with tight radii. A third consideration is that radius size and length of adjacent struts determine the order in which the struts move during crimping. Radius size refers to the radius of bends at hinge elements 232 between the struts.

In some cases, the portion of the stent at C2 (FIG. 5D) would protrude longitudinally outward, away from the other struts of the distal end ring 212D, which is considered an undesirable effect (referred to as uneven crimping). Applicant found that this effect may be minimized by adjusting the lengths of struts and adjacent bend radii, which result in the offset distances 266, 268 (between P1 and P4, and between P2 and P3).

Crests C1 and C6, at the lower end of the distal W-shape closed cell, are separated from each other by an axial distance 258, which characterizes the axial length of the marker strut 206. Crests C2 and C5, at a middle region of the distal W-shape closed cell, are separated by an axial distance 260, which is substantially less than the axial distance 258. Crests C3 and C4, at the upper end of the distal W-shape closed cell, are axially spaced apart from each other by an axial distance 262, which is equal or substantially equal to the axial distance 258.

In FIG. 5D, a circumferential line 264 is illustrated for reference in order to show the relative circumferential positions of various structural elements. It should be noted that the strut pattern of FIG. 5A-5D is illustrated flat although the stent is actually in tubular form with the circumferential line 264 encircling the central axis 224 (FIG. 2) of the stent, as partially shown in FIG. 3. The circumferential line 264 is on a plane that is perpendicular or substantially perpendicular to the central axis 224 (FIG. 2) of the stent.

The approximate locations of the troughs for the distal W-shape closed cell 236D are designated in clockwise order as T1, T2, T3 and T4. The respective circumferential positions of the troughs are indicated on the circumferential line 264 as P1, P2, P3 and P4. Troughs T1 and T4 of the distal W-shape closed cell 236D are located diametrically and axially across from each other, and their respective circumferential positions P1 and P4 do not coincide. Circumferential positions P1 and P4 are separated from each other by a circumferential distance 266. Trough T1, located on ring 212D, is located further away in terms of circumferential distance from the marker strut 206 than trough T4, located on ring 212A.

Troughs T2 and T3 of the distal W-shape closed cell 236D are located diametrically and axially across from each other, and their respective circumferential positions P2 and P3 do not coincide. Circumferential positions P2 and P3 are separated from each other by a circumferential distance 268. Trough T2, located on ring 212D, is located closer in terms of circumferential distance to the marker strut 206 and trough T3, located on ring 212A.

It is to be understood that troughs T1 and T3 are not located diametrically and axially across from each other, unlike troughs T1 and T4. Similarly, troughs T2 and T4 are not located diametrically and axially across from each other, unlike troughs T2 and T3.

In contrast to the distal W-shape closed cell, the crests of the nominal W-shape closed cell coincide with each other. That is, all of the crests of the nominal W-shape closed cell which are located on the same ring structure 212 have the same axial position. It is to be understood that in FIG. 5D the nominal W-shape closed cell is superimposed over the distal W-shape closed cell. The crests of the nominal W-shape closed cell superimposed near C1, C2 and C3 in FIG. 5D have the same or substantially the same axial position. Also, the crests of the nominal W-shape closed cell superimposed near C4, C5 and C6 have the same or substantially the same axial position.

The troughs of the nominal W-shape closed cell also coincide with each other. That is, the troughs that are located at diametrically and axially opposite positions have the same or substantially the same circumferential position. The troughs of the nominal W-shape closed cell superimposed near T1 and T4 have the same or substantially the same circumferential position. Also, the troughs of the nominal W-shape closed cell superimposed near T2 and T3 have the same or substantially the same circumferential position.

FIG. 6B shows a nominal W-shape closed cell 236 bounded in part by two rings 212M, 212N adjacent the most proximal ring 212P at the distal edge of the strut pattern 200. The nominal W-shape closed cell 236 in FIG. 5B has the same or substantially the same shape, dimensions, interior angles, and radii as the W-shape closed cells in the intermediate portion 216 of FIG. 4.

FIG. 6C shows a proximal W-shape closed cell 236P bounded in part by the most proximal ring 212P, the immediately adjacent ring 212N, and the marker strut 206 configured with two holding elements 205 for carrying a radiopaque marker bead.

The proximal W-shape closed cells 236P directly above and directly below the marker strut 206 are symmetrical about the marker strut. The proximal W-shape closed cells 236P directly above and directly below the marker strut 206 are also mirror images of each other, having the same or substantially the same shape, dimensions, interior angles, and radii.

Figure 6D:
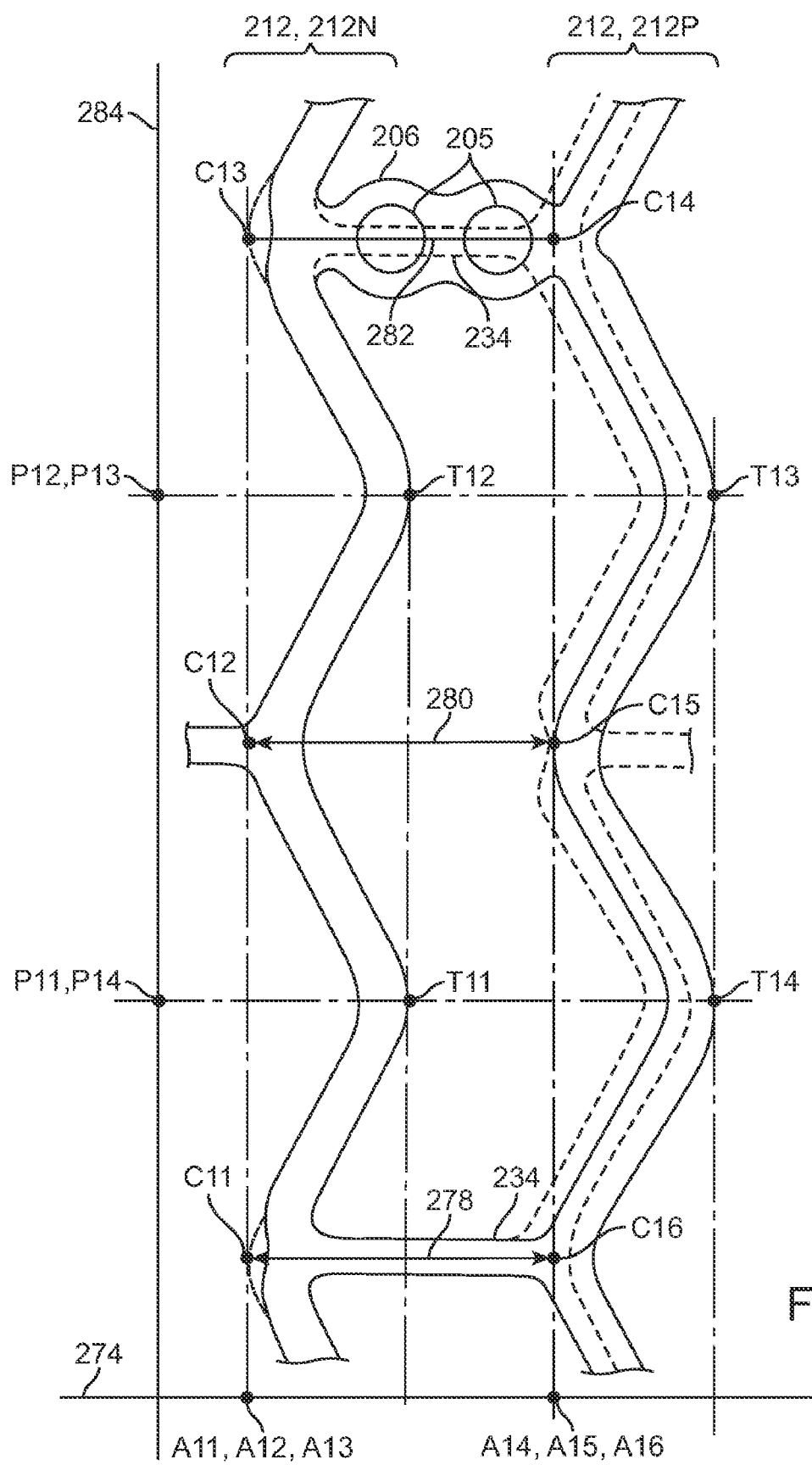
FIG. 6D is a detailed view of the strut pattern portions shown in FIGS. 6B and 6C superimposed over each other.

FIG. 6D shows the W-shape closed cells in FIGS. 6B and 6C superimposed. The struts forming the boundary of the nominal W-shape closed cell 236 in FIG. 6C are illustrated in dashed line in FIG. 6D to better show differences from the proximal W-shape closed cell 236P. It will be appreciated that the link struts 206, 234P of the proximal W-shape closed cell has a longer axial dimension than the link struts 234 of the nominal W-shape closed cell.

With continued reference to FIG. 6D, an axial line 274 is illustrated for reference in order to show the relative axial positions of various structural features. The axial line 274 is parallel or substantially parallel to the central axis 224 (FIG. 2) of the stent. The approximate locations of the crests for the proximal W-shape closed cell 236P are designated in clockwise order as C11, C12, C13, C14, C15, and C16. Crests C11, C13, C14 and C16 are approximated by dotted curved lines having the same or substantially the same radius as that at T11 and T12. The respective axial positions of the crests are indicated on the axial line 274 as A11, A12, A13, A14, A15, and A16. The axial positions A11, A12, A13 of the crests C11, C12, C13 on ring 212N coincide with each other. The axial positions A14, A15, A16 of the crests C14, C15, C16 on ring 212P coincide with each other, unlike the crests in the distal end ring 212D (FIG. 5D) which are offset due to non-uniformity of strut lengths and adjacent bend radii required to avoid uneven crimping of the distal end ring. The notch feature 290, discussed below in connection with FIG. 6E, allows the proximal end ring 212P to crimp evenly so that non-uniformity in strut lengths and adjacent radii in the proximal end ring is eliminated or reduced as compared to those in the distal end ring 212D.

Referring again to FIG. 6D, crests C11 and C16, at a lower region of the proximal W-shape closed cell, are separated from each other by an axial distance 278, which characterizes the axial length of the link strut 234P (FIG. 6C). Crests C12 and C15, at a middle region of the proximal W-shape closed cell, are separated by an axial distance 280. Crests C13 and C14, at an upper region of the proximal W-shape closed cell, are axially spaced apart from each other by an axial distance 282. The distances 278, 280, and 282 between axially opposite crests are equal or substantially equal to each other.

In FIG. 6D, a circumferential line 284 is illustrated for reference in order to show the relative circumferential positions of various structural features. It is to be understood that the strut pattern of FIGS. 6A-6D is illustrated flat although the stent is actually in tubular form with the circumferential line 284 encircling the central axis 224 (FIG. 2) of the stent, as partially shown in FIG. 3. The circumferential line 284 is on a plane that is perpendicular or substantially perpendicular to the central axis 224 of the stent. The approximate locations of the troughs for the proximal W-shape closed cell 236P are designated in clockwise order as T11, T12, T13 and T14. The respective circumferential positions of the troughs are indicated on the circumferential line 284 as P11, P12, P13 and P14.

Troughs T11 and T14, at a lower region of the proximal W-shape closed cell, are located diametrically and axially across from each other, and their respective circumferential positions P11 and P14 coincide. Trough T11, located on ring 212N, is located at the same circumferential distance from the marker strut 206 as trough T3 located on ring 212P.

Troughs T12 and T13, at an upper region of the proximal W-shape closed cell, are located diametrically and axially across from each other, and their respective circumferential positions P12 and P13 coincide. Trough T12, located on ring 212N, is located at the same circumferential distance from the marker strut 206 as trough T13 located on ring 212P.

The crests of the nominal W-shape closed cell coincide with each other in terms of axial and circumferential position. That is, all of the crests of the nominal W-shape closed cell which are located on the same ring structure 212 have the same axial position. It is to be understood that in FIG. 6D the nominal W-shape closed cell is superimposed over the proximal W-shape closed cell. The crests of the nominal W-shape closed cell superimposed near C11, C12 and C13 in FIG. 6D have the same or substantially the same axial position. The crests of the nominal W-shape closed cell superimposed near C4, C5 and C6 have the same or substantially the same axial position. It will be appreciated from comparing the dashed lines and solid lines in FIG. 6D that distances separating diametrically and axially opposite crests in the nominal W-shape closed cell (dashed line) are less than the corresponding distances of the proximal W-shape closed cell (solid line).

The troughs of the nominal W-shape closed cell also coincide with each other in terms of axial and circumferential position. That is, the troughs that are located at diametrically and axially opposite positions have the same or substantially the same circumferential position. In particular, the troughs of the nominal W-shape closed cell superimposed near T11 and T14 have the same or substantially the same circumferential position. Also, the troughs of the nominal W-shape closed cell superimposed near T12 and T13 have the same or substantially the same circumferential position.

Figure 6E:
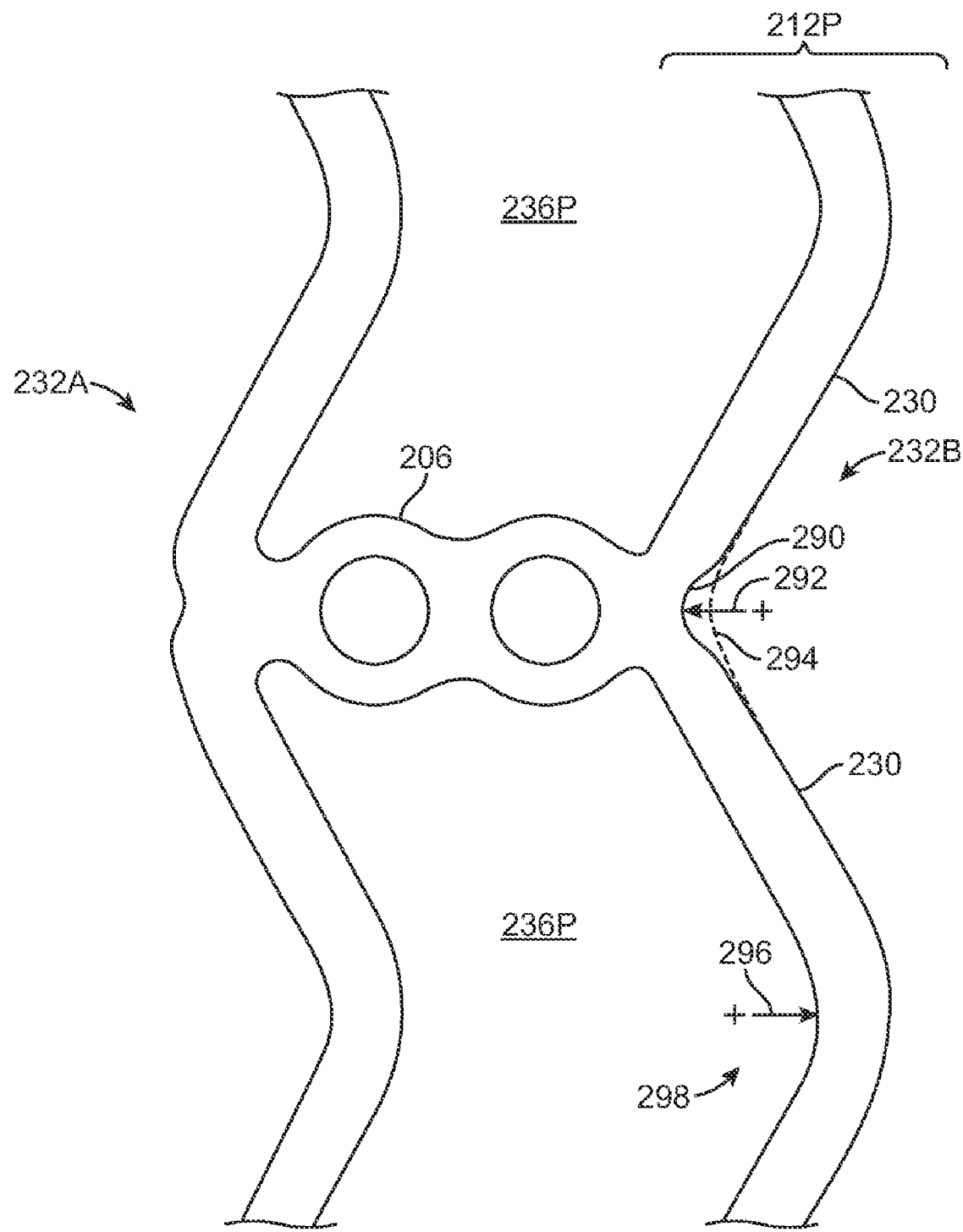
Figure 7:
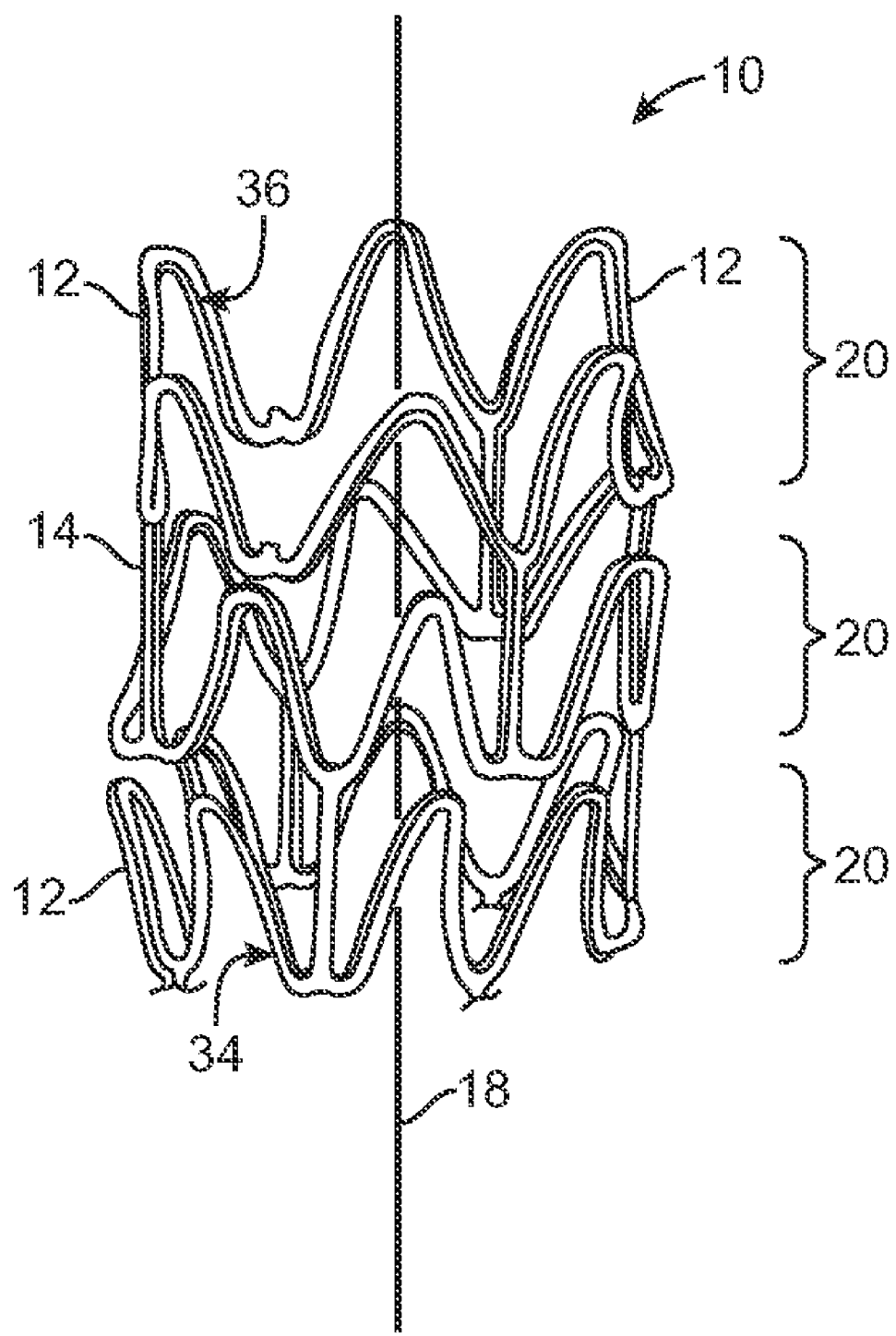
FIG. 7 is a perspective view of a portion of a stent.
Figure 8:
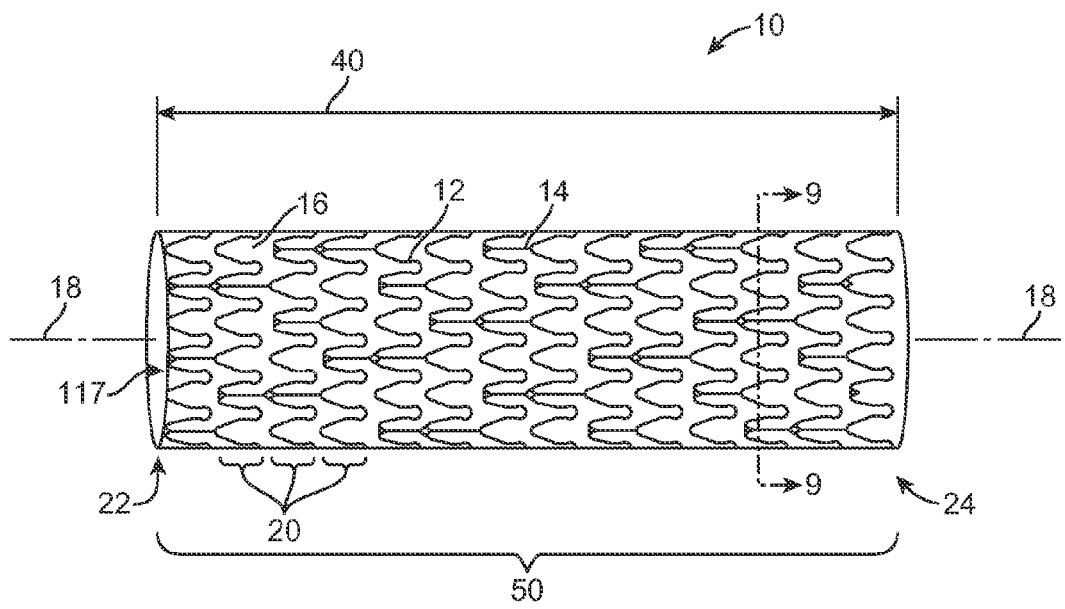
FIGS. 8 and 9 are perspective and cross-sectional views, respectively, of another stent.
Figure 9:
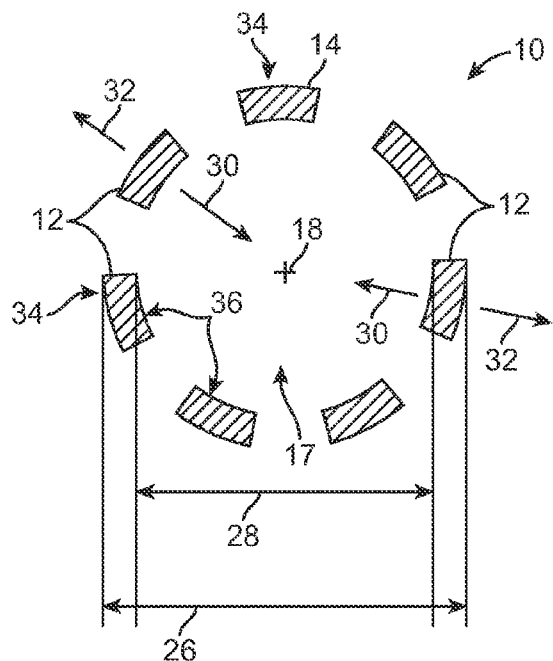

FIG. 6E shows a detail view of the marker strut 206 at the proximal end 272 (FIG. 2) of the stent. The area shown in FIG. 6E is shown in relation to the other portions of the strut pattern in FIG. 6A. There are two hinge elements 232A, 232B at opposite ends of the marker strut 206. At the proximal end of the marker strut 206, the hinge element 232B includes a feature that facilitates bending of the two immediately adjacent ring struts 230. The feature includes a notch, in the form of a curved depression 290, at the interior angle area between the two ring struts 230 that converge toward the marker strut 206. The curved depression is characterized by a radius 292. For comparison, a dotted curved 294 is shown at the interior angle area between the two ring struts 230. The dotted curve 294 has the same or substantially the same nominal radius 296 as at another interior angle area 298 on the most proximal ring 212P of the stent. The radius 292 is less than the nominal radius 296.

It will be appreciated from FIGS. 2, 3, 5A-5D and 6A-6D that the stent comprises a tubular body 300 (FIG. 3) that includes an end segment 302 and an adjacent segment 304 (FIG. 2) adjoining the end segment. The end segment 302 may be a distal end segment 302D or a proximal end segment 302P. The end segment 302 includes a series of closed cells 204 having a first W-shape 236P or 236D. The intermediate segment 304 includes a series of closed cells 204 each of which have a second W-shape 236. There is a marker strut 206 and/or linear link struts 234 at opposite ends of the individual first and second W-shapes. The marker strut 206 and the linear link struts 234 are adapted to resist compression along the axial direction. The marker strut 206 and/or linear link struts 234 at opposite ends of the first W-shape 236P or 236D are longer than linear link struts 234 at opposite ends of the second W-shape.

Referring again to FIGS. 5C-5D, a first cell from among the closed cells of the end segment includes a first crest C1 at one end of the marker strut 206 and a second crest C2 circumferentially adjacent the first crest. The first crest C1 has an axial position A1 that is axially spaced apart by an axial distance 256 from the axial position A2 of the second crest C2. The first cell further includes a third crest C3 circumferentially adjacent the second crest C2. The second crest C2 is located between the first and third crests C1, C3. The first and third crests C1, C3 have axial positions A1, A3 that coincide.

The closed cells of the end segment 302D are bounded by a first ring 212D and a second ring 212A (FIG. 5A). As shown in FIGS. 5C and 5D, the first ring 212D includes a first trough T1 and the second ring 212A includes a second trough T4 located axially across the first trough. The first trough T1 has a circumferential position P1 that is circumferentially spaced apart by a circumferential distance 266 from the circumferential position P4 of the second trough T4.

It will also be appreciated from FIGS. 2, 3, 5A-5D and 6A-6D that the stent comprises a plurality of ring structures 212, 212D, 212P that collectively form a tubular stent body 300 (FIG. 3) that has a distal end 252 (FIG. 2), a proximal end 272, and an intermediate segment 304 located between the distal and proximal ends. The ring structures are connected to each other by marker strut 206 and linear link struts 234 that are oriented axially. The ring structures and link struts form W-shape closed cells 204. The W-shape closed cells include nominal cells 236 and end cells 236D, 236P. The nominal cells 236 are located within the intermediate segment 304, and the end cells 236D, 236P are located at the distal and proximal ends 252, 272 of the stent body 300. The marker strut 206 and linear link struts 234 of the end cells are axially longer than the linear link struts 234 of the nominal cells 236.

The arrangement of ring structures 212 that form the entire stent body 300 includes two end rings 212D, 212P which are located at the distal and proximal ends 252, 272 of the stent body. Referring to FIGS. 6C and 6D, the end ring 212P at the proximal end 272 includes a first crest C14 at one end of the marker strut 206, a second crest C15 immediately adjacent the first crest, and a third crest C16 immediately adjacent the second crest. The first, second, and third crests, C14, C15, C16 have axial positions A14, A15, A16 that coincide. The end ring 212P also includes a first trough T13 and a second trough T14 immediately adjacent the first trough. The first and second troughs T13, T14 have axial positions that coincide. The ring 212N (FIG. 6C) immediately adjacent the proximal end ring 212P includes a first crest C13 at one end of the marker strut 206, a second crest C12 immediately adjacent the first crest, and a third crest C11 immediately adjacent the second crest. The first, second, and third crests, C13, C12, C11 have axial positions A13, A12, A11 that coincide. The ring 212N adjacent the proximal ring 212P also includes a first trough T12 and a second trough T11 immediately adjacent the first trough. The first and second troughs T12, T11 have axial positions that coincide.

Applicants have found that polymeric stents having strut patterns with W-shape cells that define a tubular stent body, wherein the W-shaped cells at the opposite ends of the tubular body have a modified configuration that is different than the W-shaped cells at the middle portion of the tubular body, exhibit improved stent performance over other strut patterns. An example of such a pattern exhibiting improved stent performance has been described above. The difference in shapes of the W-shaped cells at the end segments 302D, 302P, as compared to the intermediate segment, allow for even crimping and thereby avoid having portions of the end rings that protrude longitudinally outward during crimping.

Although the above embodiments have been described in terms of a stent, it will be appreciated that the present invention can be applied to endoprostheses in general. An "endoprosthesis" corresponds to an artificial device that is placed inside the body, more particularly, within an anatomical lumen. An "anatomical lumen" refers to a cavity, duct, of a tubular organ such as a blood vessel, urinary tract, and bile duct. Devices to which the present invention may be applied include without limitation self-expandable stents, balloon-expandable stents, stent-grafts, grafts.

While several particular forms of the invention have been illustrated and described, it will also be apparent that various modifications can be made without departing from the scope of the invention. For example and without limitation, the strut pattern can have a lesser or greater number of rings 212 than what is shown in FIG. 2. As a further non-limiting example, the strut pattern can have any number of W-shape closed cells circumferentially arranged to encircle the stent central axis of other embodiments of the present invention. In FIG. 2, there are three W-shape closed cells that are circumferentially arranged, although a lesser or greater number may be implemented in a strut pattern of other embodiments. In yet another non-limiting example, the strut pattern can have any number of W-shape closed cells arranged axially along the entire longitudinal length of a stent in other embodiments. In FIG. 2, there are eighteen W-shape closed cells axially arranged, although a lesser or greater number may be implemented in a strut pattern of other embodiments.

It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An endoprosthesis comprising:
   a tubular body formed of a polymer, the tubular body including an end segment and an intermediate segment adjoining the end segment, the end segment including a circumferential series of closed cells having a first W-shape, the intermediate segment including a circumferential series of closed cells having second W-shape, there being linear link struts at opposite ends of the individual first and second W-shapes, the linear link struts of the first W-shape being longer than the linear link struts of the second W-shape, wherein each of the first and second W-shapes has a perimeter that includes
 a first series of four ring struts, followed by and joined directly to one of the linear link struts, followed by and joined directly to a second series of four ring struts, and followed by and joined directly to another one of the linear link struts.

2. The endoprosthesis of claim 1, wherein one of the linear link struts within the end segment is a marker strut that includes one or more holes.

3. The endoprosthesis of claim 2, wherein a closed cell immediately adjacent to one side of the marker strut is a mirror image or is substantially a mirror image of a closed cell immediately adjacent to the opposite side of the marker strut.

4. The endoprosthesis of claim 2, wherein a first cell from among the closed cells of the end segment includes a first crest at one end of the marker strut and a second crest circumferentially adjacent the first crest, the first crest having an axial position that is axially spaced apart from the axial position of the second crest.

5. The endoprosthesis of claim 4, wherein the first cell includes a third crest circumferentially adjacent the second crest, the second crest is located between the first and third crests, and the first and third crests have axial positions that coincide.

6. The endoprosthesis of claim 1, wherein the closed cells of the end segment are bounded by a first ring and a second ring, the first ring located at a proximal end or a distal end of the tubular body, wherein the first ring includes a first trough and the second ring includes a second trough located axially across the first trough, the first trough having a circumferential position that is circumferentially spaced apart from the circumferential position of the second trough.

7. The endoprosthesis of claim 6, wherein the end segment is a distal end segment, the tubular body further includes a proximal end segment, the closed cells of the proximal end segment are bounded by a first proximal ring and a second proximal ring, the first proximal ring located at a proximal end of the tubular body, the first proximal ring includes a plurality of crests that have axial positions that coincide, the second proximal ring includes a plurality of crests that have axial positions that coincide, the first proximal ring includes a first trough and the second ring includes a second trough that is located axially across from and has an axial position that coincides with that of the first trough of the first proximal ring.

8. The endoprosthesis of claim 1, wherein the tubular body is formed of an extruded polymer tube that has been radially expanded and axially extended.

9. An endoprosthesis comprising:
ring structures made of polymer material, the ring structures forming a tubular body having a distal end, a proximal end, and an intermediate segment between the distal and proximal ends, the ring structures connected to each other by linear link struts that are oriented axially, each ring structure formed by a series of ring struts, the ring structures and link struts forming W-shape closed cells, the W-shape closed cells including nominal cells within the intermediate segment of the tubular body and end cells at the distal and proximal ends of the tubular body, the linear link struts of the end cells being axially longer than the linear link struts of the nominal cells,
wherein each of the nominal cells and the end cells has a perimeter that includes
 a first series of four of the ring struts, followed by and joined directly to one of the linear link struts, followed by and joined directly to a second series of four of the ring struts, and followed by and joined directly to another one of the linear link struts.

10. The endoprosthesis of claim 9, wherein at least one of the linear link struts located between the end cells is a marker strut that includes one or more holes sized to retain a radiopaque marker bead.

11. The endoprosthesis of claim 10, wherein an end cell located to one side of the marker strut is a mirror image or is substantially a mirror image of an end cell located to the opposite side of the marker strut.

12. The endoprosthesis of claim 10, wherein the ring structures include an end ring located at the proximal or distal end of tubular body, the end ring includes a first crest at one end of the marker strut and a second crest adjacent the first crest, the first crest having an axial position that is axially spaced apart from the axial position of the second crest.

13. The endoprosthesis of claim 12, wherein the end ring includes a third crest, the second crest is located between the first and third crests, and the first and third crests have axial positions that coincide.

14. The endoprosthesis of claim 9, wherein the ring structures include a first ring and a second ring adjacent the first ring, the first ring located at the proximal or distal end of tubular body, wherein the first ring includes a first trough and the second ring includes a second trough located axially across the first trough, the first trough having a circumferential position that is circumferentially spaced apart from the circumferential position of the second trough.

15. The endoprosthesis of claim 9, wherein:
each end cell at the distal end of the tubular body is bounded by a distal pair of ring structures, wherein each end cell at the distal end includes two crests that are located on one of the distal pair of ring structures and have axial positions that are axially spaced apart from each other, and wherein each end cell at the distal end further includes three crests that are located on the other one of the distal pair of end ring structures and have axial positions that coincide;
each nominal cell is bounded by an intermediate pair of ring structures, wherein each nominal cell includes three crests that are located on one of the intermediate pair of ring structures and have axial positions that coincide, and further includes three crests that are located on the other one of the intermediate pair of ring structures and have axial positions that coincide; and
each end cell at the proximal end of the tubular body is bounded by a proximal pair of ring structures, wherein each end cell at the proximal end includes three crests that are located on one of the proximal pair of ring structures and have axial positions that coincide, and wherein each end cell at the proximal end further includes three crests that are located on the other one of the proximal pair of ring structures and have axial positions that coincide.

16. The endoprosthesis of claim 9, wherein the ring structures are made of an extruded polymer tube that has been radially expanded and axially extended after extrusion.

17. The endoprosthesis of claim 16, wherein the hoop strength of the ring structures is increased by the radial expansion of the extruded polymer tube as compared to no radial expansion being performed to the extruded polymer tube.

18. The endoprosthesis of claim 9, wherein the ring structures are formed by a series of ring strut pairs, each pair having ring struts oriented at an interior angle relative to each other, the interior angle within a range of about 120 degrees to about 179 degrees.

19. The endoprosthesis of claim 1, wherein in each one of the perimeters:
- the four ring struts of the first series are joined to each other by three hinge elements,
- the four ring struts of the second series are joined to each other by three hinge elements, and
- each of the linear link struts is joined by a hinge element directly to the first series of ring struts and joined by a hinge element directly to the second series of ring struts.

20. The endoprosthesis of claim 9, wherein in each one of the perimeters:
- the four ring struts of the first series are joined to each other by three hinge elements,
- the four ring struts of the second series are joined to each other by three hinge elements, and
- each of the linear link struts is joined by a hinge element directly to the first series of ring struts and joined by a hinge element directly to the second series of ring struts.

* * * * *